United States Patent [19]
Dyer et al.

[11] Patent Number: 5,182,364
[45] Date of Patent: Jan. 26, 1993

[54] POLYPEPTIDE ANALOGS OF APOLIPOPROTEIN E

[75] Inventors: Cheryl A. Dyer, Poway; Linda K. Curtiss, San Diego; Richard Smith, Del Mar, all of Calif.

[73] Assignee: The Scripps Research Institute, La Jolla, Calif.

[21] Appl. No.: 485,158

[22] Filed: Feb. 26, 1990

[51] Int. Cl.$^5$ .................. C07K 7/00; A61K 37/02; A61K 37/00
[52] U.S. Cl. ..................... 530/324; 514/12
[58] Field of Search ........... 530/324; 514/12

[56] References Cited

U.S. PATENT DOCUMENTS 4,643,988  2/1987  Segrest et al. .................. 514/12

FOREIGN PATENT DOCUMENTS 0297456  4/1989  European Pat. Off. ............ 530/324

OTHER PUBLICATIONS

Segrest et al. (1974) *FEBS Lett.*, 38(3), 247–253.
Cardin et al. (1988) *Biochem. Biophys. Res. Comm.*, 154, 741–745.
Sparrow et al. (1985) *Biochemistry*, 24, 6984–6988.
Rudinger (1976) in "Peptide Hormones", ed. Parsons, pp. 1–7, Univ. Park Press, Baltimore.
Weisgraber et al. (1983) *J. Biol. Chem.*, 258, 12348–12354.
Sutcliffe et al. (1983) *Science*, 219, 660–666.
Epand et al. (1987) *J. Biol. Chem.*, 262, 9389–9396.
Gesquiere et al., *Clin. Chem.*, 31:784–785 (1985).
Mahley et al., *Biochim. Biophy. Acta.*, 737:197–222 (1983).

*Primary Examiner*—David M. Naff
*Assistant Examiner*—Jon P. Weber
*Attorney, Agent, or Firm*—Douglas A. Bingham

[57] ABSTRACT

The present invention contemplates a method for treating hypercholesterolemia in a patient, which method comprises administering to the patient an LDL plasma concentration-reducing amount of a multimeric polypeptide capable of binding the LDL receptor. The repeating unit of the polypeptide has an amino acid residue sequence corresponding to that represented by the formula LRKLRKRLLRDADDL.

1 Claim, 11 Drawing Sheets

POLYPEPTIDE ANALOGS OF APOLIPOPROTEIN E

CROSS REFERENCE TO RELATED APPLICATIONS

This is a continuation-in-part U.S. patent application Ser. No. 07/395,732, filed Aug. 18, 1989, the disclosures of which are hereby incorporated by reference.

TECHNICAL FIELD

The present invention relates to a polypeptide capable of mimicking the ability of Apolipoprotein (Apo) E to induce differentiated cellular function. More particularly, the present invention relates to a polypeptide agonist of Apo E useful for inhibiting lymphocyte proliferation and/or ovarian androgen secretion.

BACKGROUND

In 1976 it was reported that a discrete lipoprotein fraction isolated from normal human plasma inhibited mitogen- and allogenic cell-stimulated human lymphocyte proliferation in vitro (Curtiss et al., *J. Immunol.*, 116:1452, (1976)). This inhibitory plasma lipoprotein was termed LDL-In for Low Density Lipoprotein-Inhibitor because the active fraction is localized to a less dense subfraction of total LDL of density 1.006-1.063 g/ml. The characteristics of LDL-In-mediated inhibition in vitro are as follows: LDL-In has comparable inhibitory activity for phytohemagglutinin (PHA), pokeweed mitogen (PWM), and allogenic cell-stimulated human lymphocyte proliferation. The inhibitory activity of LDL-In is non-toxic and independent of mitogen concentration. Suppression by LDL-In is time dependent and approximately 18 hr of exposure of the lipoprotein to the lymphocytes before stimulation is required for maximum induction of a, stable suppressed state. LDL-In does not inhibit $^3$H-thymidine uptake when it is added to the cultures 18-20 hr after stimulation, suggesting that this lipoprotein influences metabolic events associated with an early inductive phase of lymphocyte activation.

The immunosuppressive activity of LDL-In has been studied in a number of systems both in vitro and in vivo. To summarize, in vitro activities of LDL-In include suppression of: a) mitogen stimulated $^3$H-thymidine uptake, Curtiss et al., *J. Immunol.*, 116:1452, (1976), b) allogenic cell-stimulated $^3$H-thymidine uptake (Curtiss et al., *J. Immunol.*, 116:1452, (1976), Curtiss et al., *J. Immunol.*, 118:1966, (1977), c) the primary generation of cytotoxic T cells (Edgington et al., *Regulatory Mechanisms in Lymphocyte Activation: Proceedings of the Eleventh Leukocyte Culture Conference.*, D.O. Lucas, ed. Academic Press, New York, pp. 736, (1977)), d) pokeweed mitogen stimulated immunoglobulin synthesis (Curtiss et al., *J. Clin. Invest.*, 63:193, (1979)), and e) B-cell Epstein Barr Virus transformation (Chisari et al., *J. Clin. Invest.*, 68:329, (1981)). In vivo LDL-In has been shown to inhibit: a) the primary humoral immune response to sheep red blood cells (Curtiss et al., *J. Immunol.*, 118:648, (1977), DeHeer et al., *Immunopharmacology*, 2:9, (1979), Curtiss et al., *Cell. Immunol.*, 49:1, (1980)), b) the primary generation of cytotoxic T-cells (Edgington et al., *Regulatory Mechanisms in Lymphocyte Activation: Proceedings of the Eleventh Leukocyte Culture Conference.*, D.O. Lucas, ed. Academic Press, New York, pp. 736, (1977)), and c) immunologic attention of tumor growth (Edgington et al., *Cancer Res.*, 41:3786, (1981), Edgington et al., *Dietary Fats and Health.*, ACOS Monograph No. 10, Perkins and Visek, eds., pp. 901, (1981)).

The effects of lipoproteins on immune cell function in vivo are exceedingly complex. A major finding of the investigation of the physiologic implications of immunosuppression by LDL-In in vivo is that the observed functional outcome is strikingly dose dependent. This important concept is best illustrated by describing in more detail studies of the effects of LDL-In on the survival of experimental animals challenged with syngeneic tumors (Edgington et al., *Cancer Res.*, 41:3786, (1981), Edgington et al., *Dietary Fats and Health.*, ACOS Monograph No. 10, Perkins and Visek, eds., pp. 901, (1981)). Seemingly divergent effects of LDL-In are observed on the growth of the syngeneic SaD2 fibrosarcoma in DBA/2 mice. The growth of $1 \times 10^5$ viable tumor cells in control mice without immunoprotection (i.e., 10-days prior immunization with $10^{-6}$ irradiated tumor cells) is detectable at 25 days and proceeds rapidly until death at about 43 days. In contrast, tumor growth is slower in immunoprotected mice. This tumor growth is characterized by a reduction in tumor mass of at least a half and no deaths by day 60. Intravenous administration of high doses of LDL-In 24 hr before immunoprotection with killed tumor cells abolishes the protective effect of immunization. This dose corresponds to a dose that is required to abolish both B-cell and T-cell effector cell functions. The administration of an intermediate dose of LDL-In before immunoprotection with the killed tumor cells has no discernable effect on the subsequent growth of the viable tumor cell challenge. In contrast, intravenous administration of even lower doses of LDL-In 24 hr before immunoprotection with killed tumor cells results in the enhancement of tumor rejection and host survival. This dose of LDL-In is concordant with the dose required for selective inhibition of suppressor cell function in vitro (Curtiss et al., *J. Clin. Invest.*, 63:193, (1979)). Thus, depending upon the amount of immunoregulatory lipoprotein that a particular lymphocyte population is exposed to in vivo, very different functional outcomes will result.

Lipoproteins are cleared from the plasma by binding to high-affinity receptors on liver cells and extrahepatic tissues such as the adrenal glands and ovaries (Kowal, R.C. et al., *Proc. Natl. Acad. Sci. USA*, 86:5810-5814, (1989). Two distinct sets of receptors bind APO E-containing lipoproteins. The low density lipoprotein (LDL) receptor [Yamamoto et al., *Cell*, 39:27-38 (1984)], 70% of which are thought to be located on hepatic cells, binds very low density lipoproteins (VLDL) and Apo E-containing remnants of chylomicrons. The existence of a second set of LDL-receptors, termed "remnant receptors", is inferred from studies showing that the plasma clearance of APO E-containing chylomicron remnants occurs at normal rates in animals with genetically defective LDL-receptors. Recently, an LDL-receptor-related protein (LRP) has been found on the surface of hepatic cells. Herz et al., *EMBO*, 7:4119-4127 (1988). LRP shares cysteine-repeat sequences with LDL and has been shown to bind and mediate the extracellular clearance of APO E-containing lipoproteins (Kowal, R.C. et al. *Proc. Natl. Acad. Sci. USA*, 86:5810-5814, (1989).

Plasma lipoproteins differ from most humoral immunoregulatory molecules in that they are large heterogenous non-covalent complexes of lipid and protein.

An important step to understanding the mechanism of lipoprotein regulation of cell function is an identification of the constituent(s) of the lipoprotein particle that mediate the observed biologic effects. Plasma lipoproteins contain various amounts of apoproteins, glyceride, free and esterified cholesterol, phospholipid, glycolipid and free fatty acid. Many of these constituents of lipoproteins can by themselves influence cell function.

The heterogeneity of apoproteins in terms of structure, exposure and function make them likely candidates as biologically important constituents of LDL-In, and the contribution of the apoproteins to biologic activity has been extensively studied. LDL-In contains Apo B, Apo E, and each of the C apoproteins. The specific role played by Apo B and Apo E in LDL-In was investigated immunochemically using Apo B-specific and Apo E-specific monoclonal antibodies (Curtiss et al., Fed. Proc., 40:348, (1981), Curtiss et al., Atherosclerosis, 2(5):A111, (1982)). Some, but not all, of the Apo B-antibodies and each of the Apo E-specific antibodies bind and facilitate the indirect precipitation and removal of the inhibitory activity of LDL-In from a lipoprotein fraction. These results indicate that LDL-In contains both apoproteins B and E, but they do not identify which apoprotein is important to or required for activity.

Further substantiation that Apo E and Apo B-containing lipoproteins are important regulators of lymphocyte function has come from studies of the inhibitory properties of fetal cord blood plasma lipoproteins (Curtiss et al., J. Immunol., 133:1379, (1984)). In these studies a direct correlation between Apo E and inhibition was established. Cord blood lipoprotein concentrations are lower than those of adult, i.e., the low density lipoprotein (LDL) level in cord blood is 30% that of adult, whereas the high density lipoprotein (HDL) level is 50% of adult levels. In contrast, the Apo E concentration in fetal cord blood is 2-fold higher than adult (Curtiss et al., J. Immunol., 133:1379, (1984)). Therefore, the capacity of LDL and HDL to inhibit mitogen-stimulated $^3$H-thymidine uptake in adult peripheral blood mononuclear cells was used as an in vitro system to study immunosuppression. Relative to adult lipoproteins, cord blood LDL and HDL are 2 to 4 times more potent in inhibiting cellular proliferation. Radioimmunoassay results demonstrate a strong correlation between the amount of Apo E in cord blood LDL and HDL and the inhibition of cell proliferation. Furthermore, selective removal of Apo E-containing lipoproteins decreases the inhibitory capacity of cord blood LDL and eliminates almost completely inhibition by HDL. The results indicate that cord blood lipoproteins containing Apo E in association with either LDL or HDL can suppress the immune response (Curtiss et al., J. Immunol., 133:1379, (1984)). The fetus is an allograft to its mother. Therefore the relatively high fetal levels of Apo E may have functional significance in the establishment of self as well as maintenance of the fetus in utero.

More recently, the inhibitory activity of isolated (lipid-free) Apo E has been studied. Immunosuppression was measured as inhibition of $^3$H-thymidine uptake by peripheral blood mononuclear cells (PBM) with phytohemagglutinin (PHA). Apo E isolated from lipoproteins had good activity (i.e., approximately 15 ug/ml was required for 50% inhibition, and maximal inhibition occurred at 20 ug/ml), whereas fractions containing the lipid-free C apoproteins were not inhibitory at >20 ug/ml (Pepe et al., J. Immunol., 126:3716, 1986)). Suppression of lymphocyte proliferation by the native lipoprotein, LDL-In, is irreversible and has distinguishable temporal requirements (Curtiss et al., J. Immunol., 116:1452, (1976), Curtiss et al., J. Immunol., 118:1966, (1977)). Suppression by isolated Apo E is identical. That is, cells exposed to isolated Apo E for 24 hr and washed free of non-cell associated Apo E before mitogen stimulation, remain fully suppressed. And, maximal inhibition is obtained with either LDL-In or Apo E only after a 24 hr exposure of the cells before the addition of mitogen. Exposure periods of 18 hr or less result in little or no suppression by either inhibitor. Furthermore, cells receiving inhibitors or PHA simultaneously, or cells receiving either inhibitor after PHA exposure, are fully capable of responding to mitogen induction, suggesting that neither LDL-In nor Apo E are directly toxic. The irreversibility and temporal requirements of suppression confirm that Apo E isolated from lipoproteins has the same characteristics of immunosuppression as LDL-In and that an active moiety of LDL-In is Apo E (Pepe et al., J. Immunol., 126:3716, (1986)).

Cardin et al., Biochem. Biophys Res. Comm., 154:741-745 (1988) reported that a polypeptide portion of Apo E having an amino acid residue sequence identical to that of Apo E residues 141-155 inhibits lymphocyte proliferation when coupled to bovine serum albumin (BSA). However, conspicuously absent from the study of Cardin et al. was any control for cell viability allowing for a determination of whether or not the inhibition observed was due to cytotoxicity of the peptide-BSA conjugate.

By way of further background, Dyer et al., J. Biol. Chem., 263:10965-10973 (1988) reported that isolated lipid free rat Apo inhibits androgen production by the ovarian theca and interstitial cells induced by the gonadotropin, luteinizing hormone (LH).

BRIEF SUMMARY OF THE INVENTION

It has now been discovered that the amino acid residue sequence corresponding to residues 141-155 of mature Apo E can mimic the biological activity of Apo E only when present as a multimeric peptide or a self-conjugate. It has also been discovered that the inhibitory effect on lymphocyte proliferation by peptide-BSA conjugates where the peptide has an amino acid residue sequence corresponding to residues 141-155 of Apo E is not physiologically specific but rather due to cytotoxicity.

Thus, the present invention contemplates a polypeptide analog of Apo E characterized by a plurality of segments each having an amino acid residue sequence corresponding to residues 141-155 of Apo E, e.g., (LRKLRKRLLRDADDL)$_a$ where a is an integer of at least 2 indicating the number of times the sequence within parenthesis is present within the primary structure of the polypeptide. In a preferred embodiment, the present invention contemplates a tandem peptide representing two repeats of the 141-155 sequence.

In another embodiment, the present invention contemplates an isolated self-conjugate, i.e., polypeptides having corresponding amino acid residue sequences operatively linked to each other by other than a peptide bond between the alpha-amino group and carboxy group of contiguous amino acid residues. The conjugate contains a plurality of operatively linked polypeptides having amino acid residue sequences corresponding to the sequence of Apo E residues 141-155.

The polypeptides and conjugates of the present are useful agents for modulating differentiated cell function, such as lymphocyte proliferation, ovarian androgen production, LDL binding and degradation, and the like. Therapeutic compositions containing a polypeptide or conjugate of this invention in a pharmaceutically acceptable excipient, typically in unit dose form, are also contemplated for modulating differentiated cell function.

DETAILED DESCRIPTION OF THE INVENTION

A. Definitions

Figure 1:
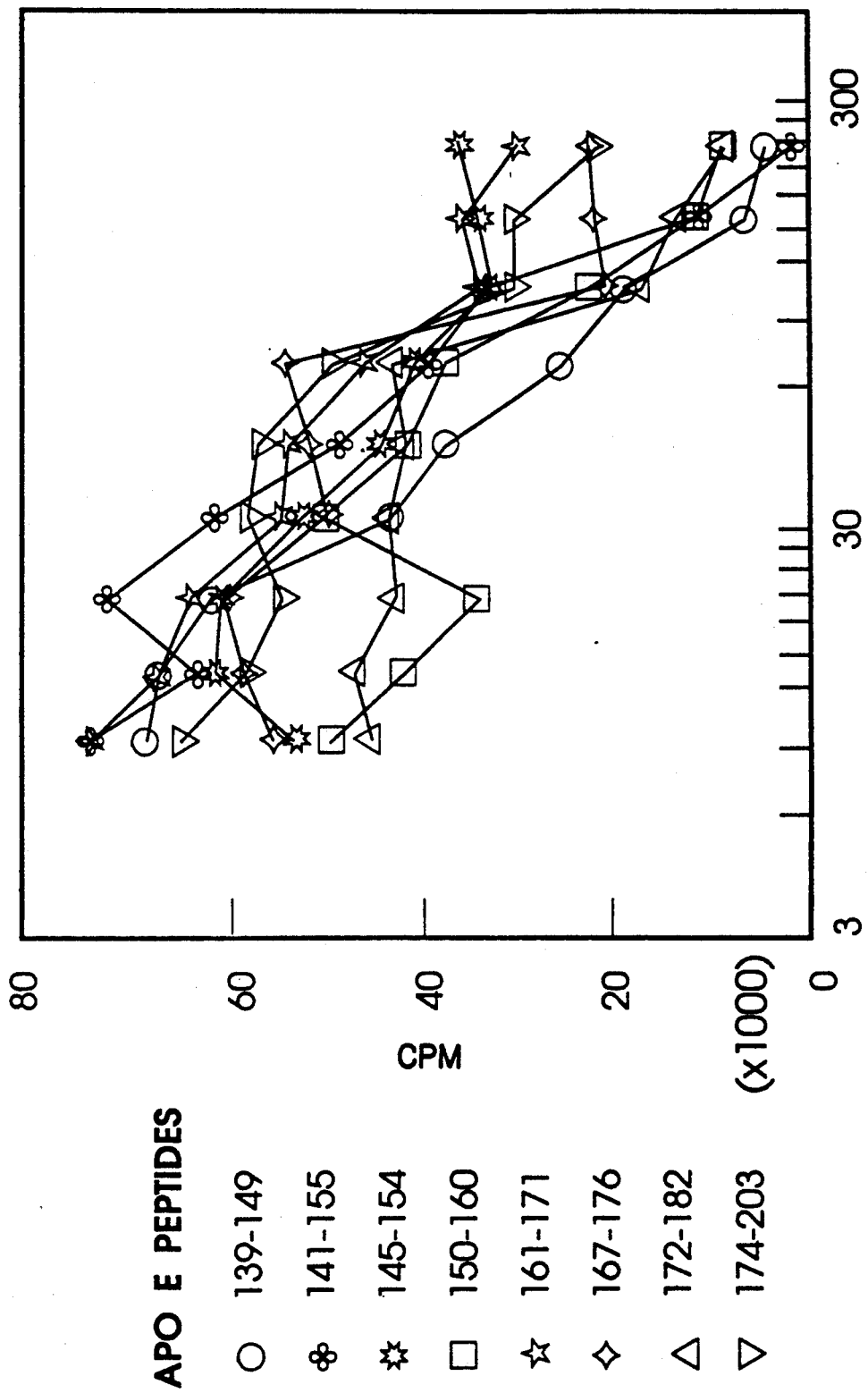
FIG. 1 illustrates that all Apo E peptide-BSA conjugates inhibited lymphocyte proliferation in an approximately equivalent manner, thereby indicating a lack of specificity. Increasing concentrations of Apo E peptide-BSA conjugates were added to cultures that contained $1 \times 10^6$ peripheral blood mononuclear cells per ml. The cells were cultured at 37° C. in RPMI with 5% fetal bovine serum. All cells were exposed to PHA at 24 hr. Each point represents the average $^3$H-thymidine uptake, measured in counts per minute (cpm), of four wells per treatment and the standard error was less than 10% for all points.

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Protein: refers to a linear series of greater than 50 amino acid residues connected one to the other as in a polypeptide.

Synthetic peptide: refers to a chemically produced chain of amino acid residues linked together by peptide bonds that is free of naturally occurring proteins and fragments thereof.

B. Apo E Polypeptide Analogs

The present invention contemplates a polypeptide capable of substantially mimicking the ability of Apo E to induce differentiated cellular function, such as hepatic LDL degradation, lymphocyte proliferation, androgen secretion by ovarian theca and interstitial cells, and the like. That is, a subject polypeptide acts as an analog of Apo E at least with regard to the ability of Apo E to inhibit lymphocyte proliferation and/or ovarian androgen secretion, and increase the uptake of LDL by hepatocytes.

A subject polypeptide is further characterized by the presence of a plurality of Apo E-derived segments (regions) within the polypeptide's primary structure, each of the segments being defined by a sequence of amino acid residues corresponding to the formula:

Leu-Arg-Lys-Leu-Arg-Lys-Arg-Leu-Leu-Arg-Asp-Ala-Asp-Asp-Leu.

The Apo E-derived segments are capable of binding to the LDL-receptor and/or LDL-receptor-related protein [Herz et al., *EMBO Journal*, 7:4119–4129 (1988)] as evidenced by the ability of the binding to be competitively inhibited. The Apo E-derived segments can be adjacent and/or contiguous within the polypeptide chain, with adjacent segments being separated in the amino acid residue sequence of the polypeptide by one or more spacing residue. Preferably, the spacing residues make up a spacing segment in the range of about 1 to about 20, preferably about 5 to about 15, and more usually about 10, amino acid residues in length.

In addition, a subject polypeptide can contain a leader segment of 1 conveniently up to about 33, such as about 11, about 18 or about 22, amino acid residues located amino-terminal to the amino-terminal Apo E-derived or spacing segment.

In a similar manner, a subject polypeptide need not end with the carboxy-terminal residue of an Apo E-derived segment or spacer segment. A carboxy terminal tail segment can be present containing 1 conveniently up to about 33, such about 11, about 18 or about 22, amino acid residues.

Preferred polypeptides of the present invention are therefor defined by formula I:

B-(X$_n$-Leu-Arg-Lys-Leu-Arg-Lys-Arg-Leu-Leu-Arg-Asp-Ala-Asp-Asp-Leu-Z$_m$)$_a$-J,

In the above formula, B is an amino-terminal NH$_2$ group or a previously discussed leader segment; J is a carboxy-terminal COOH group or a previously discussed tail segment; X and Z are first and second, respectively, spacing segments whose amino acid residue sequences can be the same or different; n is either 1 or 0 such that when n is 1, X is present, and when n is 0, X is not present; m is either 1 or 0 such that when m is 1, Z is present, and when m is 0, Z is not present; and a is an integer from 2 to about 10, more preferably 2 to about 5 and usually 2 to 3, indicating the number of times the amino acid residue sequence in parenthesis is present (repeated) in the polypeptide primary structure. Preferably, the sequence in parenthesis corresponds in its entirety, and preferably is identical to, a portion of the amino acid residue sequence of Apo E. Preferred polypeptides are those whose formulas are shown in Table 1.

TABLE 1

| Designation | Amino Acid Residue Sequences |
|---|---|
| p(141-155)$_2$ | LRKLRKRLLRDADDLLRKLRKRLLRDADDL |
| p(129-163)$_2$ | STEELRVRLASHLRKLRKRLLRDADDLQKRLAVYQSTEELR-VRLASHLRKLRKRLLRDADDLQKRLAVYQ |

1. It should be noted that p(129-163)$_2$ contains a 12 residue leader segment (residues 1-12), a 20 residue spacing segment (residues 28-47) and an 8 residue tail segment (residues 63-70). The designation p(141-155)$_2$ defines a tandem Apo E peptide which contains two adjacent sequences of the p141-155 segment. Preferred also are self-conjugates of the tandem APO E peptides designated p(141-155)$_2$ - p(141-155)$_2$.

A subject polypeptide typically contains a total of about 30 to about 450 amino acid residues, preferably about 60 to about 120 residues. Typically, a subject polypeptide contains no more than about 100, preferably no more than about 70 and usually no more than about 30 or 40 amino acid residues in its primary sequence.

A subject polypeptide includes any analog, fragment or chemical derivative of a polypeptide whose amino acid residue sequence is shown herein so long as the polypeptide is capable of inducing differentiated cellular function in a manner corresponding to that of Apo E. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability to mimic Apo E as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

A subject polypeptide can be prepared using recombinant nucleic acid methodologies well known in the art. For instance, DNA sequences useful in producing a subject polypeptide are described in Paik et al., *Proc. Natl. Acad. Sci. USA*, 82:3445-3449, (1985); McLean et al., *J. Biol. Chem.*, 259:6498-6504, (1984); and Rall et al., *J. Biol. Chem.*, 257:4171-4178, (1982). A DNA segment coding for a polypeptide of this invention can be synthesized by chemical techniques, for example the phosphotriester method of Matteucci et al., *J. Am. Chem. Soc.*, 103:3185, (1981). The DNA segment can then be ligated into an expression vector, and a host transformed therewith can be used to produce the polypeptide. See, for example, *Current Protocols In Molecular Biology*, Ausubel et al., eds., John Wiley & Sons, New York, N.Y.; U.S. Pat. Nos. 4,237,224 and 4,356,270.

The recombinant expression vectors capable of expressing a subject polypeptide and methods of their use for producing a subject polypeptide are contemplated as part of the present invention.

A subject polypeptide can also be prepared using the solid-phase synthetic technique initially described by Merrifield, in *J. Am. Chem. Soc.*, 85:2149-2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104-237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

C. Conjugates

The present invention further contemplates an Apo E analog in the form of a polypeptide conjugate comprised of a plurality of polypeptides operatively linked, by other than a peptide bond between the alpha-amino group and carboxy group of contiguous amino acid residues, where at least two of the linked polypeptides have an amino acid residue sequence corresponding to that represented by the formula:

B-($X_n$-Leu-Arg-Lys-Leu-Arg-Lys-Arg-Leu-Leu-Arg-Asp-Ala-Asp-Asp-Leu-$Z_m$)$_a$-J, wherein B, X, Z, J, n, m and a are defined as previously discussed except that a can also be the integer 1.

Preferred self-conjugates are p141-155 linked to p141-155, designated (p141-155)-(p141-155) and p129-163 linked to p129-163, designated (p129-163)-(p129-163).

In preferred embodiments, a conjugate of this invention has a molecular weight of less than about 40,000 daltons, preferably less than about 20,000 daltons, and more preferably less than about 10,000 daltons. Typically, a subject conjugate has a molecular weight of no more than about 15,000 daltons, preferably no more than about 8,000 daltons, and usually no more than about 4,000 daltons. Preferably, the conjugate is dimeric or trimeric, i.e., consists essentially of two or three polypeptide chains, respectively.

A polypeptide conjugate of this invention is further characterized by its ability to substantially mimic Apo E's ability to induce differentiated cellular function, such as lymphocyte proliferation, ovarian androgen secretion, and the like. The subject conjugates are also substantially free of toxicity toward lymphocytes and androgen-producing ovarian (theca/interstitial) cells at concentrations of about 20 micrograms per milliliter (ug/ml).

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. Nos. 4,493,795, 3,791,932 and 3,839,153. In addition, a site directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

TABLE 2

| Designation[1] | Amino Acid Residue Sequence |
|---|---|
| p93-112 | LSKELQAAQARLGADMEDVR |
| p139-149 | SHLRKLRKRLL |
| p141-155 | LRKLRKRLLRDADDL |
| p145-154 | RKRLLRDADD |
| p150-160 | RDADDLQKRLA |
| p161-171 | VYQAGAREGAE |
| p167-176 | REGAERGLSA |
| p172-182 | RGLSAIRERL |
| p174-203 | LSAIRERLGPLVEQGRVRAATVGSLAGQPL |

[1]The designation for each peptide indicates the position within the amino acid residue sequence of the mature Apo E protein to which the peptide sequence corresponds, i.e., is derived from.

D. Compositions for Modulating Hepatic LDL Degradation

In view of the ability of the polypeptides and conjugates of the present invention to bind the LDL-receptor present on hepatocytes, the present invention contemplates a composition for modulating hepatic uptake of LDL. The composition comprises an LDL-receptor binding moiety operatively linked to an LDL binding moiety. The LDL-receptor binding moiety comprises a polypeptide and/or conjugate of the present invention. A preferred LDL-receptor binding moiety comprises the polypeptide segment designated P (141–155)$_2$ whose amino acid residue sequence is shown in Table 1.

The LDL-receptor binding moiety can be operatively linked to the LDL binding moiety by a peptide bond or through a covalent bond that is not a peptide bond between the alpha-amino group and carboxyl group of continuous amino acid residues.

An LDL binding moiety can be an anti-LDL antibody molecule or immunologically active fragment thereof. Exemplary anti-LDL-antibody molecules are produced by the following hybridomas, all of which have been deposited with the *American Tissue Culture Collection* (Rockville, Md.): HB8744, HB8745, and HB8741, all of which produce anti-Apo-A-I antibody molecules, and HB8746 and HB8742, both of which produce anti-Apo B-100 antibody molecules. The LDL-receptor binding polypeptide and/or conjugate of this invention can be chemically coupled as described hereinbefore to the anti-LDL antibody molecule. Alternatively, a polypeptide of this invention can be incorporated into the primary amino acid residue sequence of the antibody molecule by recombinant DNA techniques. Typically, the LDL-receptor binding polypeptide will be incorporated into or substituted for a portion of one of the antibody molecule's constant domains. See U.S. Pat. Nos. 4,816,567, 4,816,397 and 4,647,334.

In preferred embodiments, the LDL binding moiety is a lipophilic (hydrophobic) sequence of amino acid residues. More preferably, the LDL binding moiety is a polypeptide segment having an amino acid residue sequence capable of forming an amphipathic helix.

Of course, when the means for operatively linking the LDL-receptor moiety and LDL binding moiety is other than a peptide bond, the linking typically occurs between amino acid residue chains on residues at or near the carboxy-and/or amino-terminus of the respective moieties so as to preserve their activities.

Preferred helical amphipathic polypeptide segments of this invention, whether incorporated into the composition by a peptidic or non-peptidic bond, include those having an amino acid residue sequence corresponding to that of an apolipoprotein, such as Apo B-100, Apo B-48, Apo C-I, Apo C-II, Apo C-III, Apo A-I, Apo A-II, Apo D, Apo E and the like. See, Fitch, Genetics, 86:623-644 (1977); Segrest et al., Biopolymers, 16:2053-2065 (1977); and Chan, Klin Wochenscher, 67:225-237 (1989). By using a helical amphipathic polypeptide segment with amino acid residue sequence derived from Apo B-100 or Apo B-48, the polypeptide can be preferentially targeted to LDL as opposed to other lipoprotein species.

The amphipathic helix is characterized by a spacial segregation of hydrophobic and hydrophilic amino acid residues on opposite faces of the helix. The clustered nonpolar residues can then intercalate into lipid particles such as LDL. In addition to this hydrophobic interaction, there may also be specific charge interactions between lipid and peptide. For example, it has been demonstrated that an 18-residue peptide can bind to phospholipid if it has positively charged residues at the hydrophobic-hydrophilic interface of an amphipathic helix and negatively charged residues opposite the hydrophobic face of the helix. See Epand et al., *J. Biol. Chem.*, 264:4628-4635 (1989).

A particularly preferred helical amphipathic polypeptide segment useful in binding the Apo E-derived polypeptide segment (LDL-receptor binding moiety to LDL has an amino acid residue sequence corresponding to the formula:
EWLKAFYEKVLEKLKELF.

In preferred embodiments, the composition is a polypeptide according to formula I wherein B and/or J is a helical amphipathic polypeptide segment as described above. One preferred polypeptide of this type has an amino acid residue sequence corresponding to the formula:
LRKLRKRLLRDADDLLRKLRKRLLRDADDL-EWLKAFYEKVLEKLKELF.

In preferred embodiments, the subject polypeptide or conjugate is dispersed in a carrier, such as a phospholipid. More preferably, the subject polypeptide or conjugate is removeably inserted in a liposome, i.e., it is incorporated (anchored) into the liposome bilayer via the LDL binding moiety. See, for example, Gregoriadis, *Trends in Biotech.*, 3:235-241 (1985) and Eriksson et al., pg 141-156 in *Liposome Technology* Vol. II, ed G. Gregoriadis CRC Press, Boca Raton, Fla.

E. Therapeutic Methods

The polypeptides, conjugates and compositions contemplated by the present invention are useful as agents for modulating those physiologic events induced by native Apo E, such as immune response, steroidogenesis and/or LDL binding. For instance, a polypeptide and/or conjugate of this invention can be used as an immunosuppressive agent to inhibit the proliferation of lymphocytes or as an agent to inhibit ovarian androgen production. The polypeptide and/or conjugate is administered to the animal, such as a human, in need of such treatment, in a predetermined amount calculated to achieve the desired effect, i.e., in a therapeutically effective amount.

For instance, when used as an immunosuppressive agent for inhibiting lymphocyte proliferation, such as in a patient displaying the symptoms of an autoimmune disease, the polypeptide and/or conjugate is administered in an amount sufficient to achieve a plasma concentration of at least about 0.8 ug/ml, preferably at least about 1.0 ug/ml, more preferably at least about 2 ug/ml, and usually 3 or 4 ug/ml.

In some cases, it is desirable to apply the subject polypeptide and/or conjugate locally as an immunosuppressive agent. For instance, about 10 ug to about 1 mg can be applied by injection into an arthritic joint (e.g., into the synovial fluid of the joint) to suppress inflammation.

When used as an agent for inhibiting ovarian androgen production, such as in females having polycystic ovaries, the polypeptide and/or conjugate of this invention is administered in an amount sufficient to achieve a plasma concentration of at least about a 2 ug/ml, preferably about 5 ug/ml, and more preferably about 10 ug/ml.

When the tandem Apo E peptide p(141-155)$_2$ or its self conjugate is used to inhibit lymphocyte proliferation, the peptide or its conjugate is administered in an amount sufficient to achieve a plasma concentration of at least about 8 mg/ml, preferably at least 10 mg/ml, and more preferably at least 15 mg/ml. When used to enhance lymphocyte proliferation, the peptide or its conjugate is given in an amount sufficient to achieve a plasma concentration of from about 2 mg/ml to about 6 mg/ml, preferably from about 3 mg/ml to about 5 mg/ml.

When the tandem Apo E peptide p(141-155)$_2$ or its self conjugate is used to inhibit ovarian androgen production, the peptide or its conjugate is administered in an amount sufficient to achieve a plasma concentration of at least about 0.6 mg/ml, preferably at least 1.0 mg/ml, and more preferably at least 8 mg/ml. When used to enhance ovarian androgen production, the peptide or its conjugate is given in an amount sufficient to achieve a plasma concentration of from about 0.1 mg/ml to about 0.4 mg/ml, preferably from about 0.2 mg/ml to about 0.3 mg/ml.

When a composition contains either tandem Apo E peptide p(141-155)$_2$ or its self conjugate operatively linked to an LDL binding moiety is used to enhance hepatic LDL binding and uptake, as in subjects with hyper-cholesterolemia, the composition is administered in an amount sufficient to achieve a tandem peptide or conjugate plasma concentration of at least about 20 mg/ml, preferably at least about 50 mg/ml, and more preferably at least about 100 mg/ml.

The preparation of therapeutic compositions which contain polypeptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-containing compositions are conventionally administered intravenously or at the site of autoimmune-induced inflammation, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition of lymphoproliferation or androgen production desired. Precise amounts of active ingredient required to be administered depend on the judgment of the practitioner and are peculiar to each individual. However, suitable dosage ranges for systemic application are of the order of 0.01 to 10, preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

EXAMPLES

The following examples are intended to illustrate, but not limit, the present invention.

1. Polypeptide And Conjugate Preparation (a) Synthesis

The polypeptide $p(141-155)_2$ and those shown in Table 2, were synthesized using the classical solid-phase technique described by Merrifield, *Adv. Enzymol.*, 32:221-96, (1969) as adapted for use with a model 430A automated peptide synthesizer (Applied Biosystems, Foster City, Calif.). Polypeptide resins were cleaved by hydrogen fluoride, extracted and analyzed for purity by high-performance liquid chromatography (HPLC) using a reverse-phase C18 column manufactured by Waters Associates, Milford, Mass.

(b) Self-Conjugation Of Apo E Peptides p141-155 And p129-163

The synthetic peptides containing the amino acid residues 141-155 or 129-163 of Apo E or the tandem $p(141-155)_2$ were self-conjugated (i.e., p141-155 was coupled to p141-155 and p129-163 was coupled to p129-163) according to the procedure of Hoare et al., *J. Biol. Chem.*, 242:2447, (1967). Briefly, 100 mg of synthetic peptide was dissolved in 10 ml of high purity water (Nanopure system). One gram of EDG [1-ethyl-3-(3-dimethylaminopropyl) carbodiimide hydrochloride] was admixed to the peptide solution. The reaction proceeds rapidly at room temperature and is complete after one hour. During the first five to ten minutes the pH of the reaction admixture is monitored. The starting solution, before the addition of EDG, is at a pH of approximately 3.7. Upon the addition of EDG, the pH increases to approximately 5.0 in the first five minutes. At five minutes, 50 ul of 0.1N HCL is added. No further addition of acid is necessary during the rest of the incubation. The admixture is rotated while incubating to insure complete reaction. The reaction is quenched with 10 ml of 2M acetate buffer, pH 4.75.

To isolate conjugated (operatively linked) peptides from unreacted peptide and chemicals, the self-conjugation preparation is dialyzed in 2,000 molecular weight cut-off dialysis tubing, 18 millimeter wide and approximately two times the length of the sample volume. Starting dialysis is done against 2M acetic acid. A gradient reducing the concentration of acetic acid from 2M to <0.01M is achieved by changing the dialysis buffer (one liter) every hour stepping down the concentration of acetic acid by 50% at each change. Once the acetic acid concentration has been lowered to <10mM, the sample is then dialyzed against one liter highly purified water over night at room temperature with at least five one liter changes. The sample is lyophilized to dryness and redissolved in phosphate-buffered saline (PBS) and is ready for addition to cell culture.

The yield of self-conjugated peptide from this procedure is low, usually not greater than 5%. For instance, in one conjugation starting with 100 mg of synthetic peptide, 2.82 mg of p141-155 self-conjugated peptide was recovered. The polypeptide concentration of the peptide redissolved in PBS was determined by the Lowry protein assay method. All additions of peptide to cell culture of this self-conjugated preparation were based on the value from Lowry assay. The activity in the self-conjugated p141-155 preparation is stable for at least two months when stored at −20° C.

2. Monomeric Peptides And Peptide-BSA Conjugates Do Not Specifically Inhibit Lymphocyte Proliferation A lymphocyte cell culture system was used to examine the ability of various polypeptides and conjugates to mimic the ability of Apo E to inhibit lymphocyte differentiation as evidence by proliferation.

Human peripheral blood mononuclear (PBM) cells are isolated from whole blood on a Ficoll-Hypaque gradient. The collected PBMs are washed three times with fresh medium (RPMI-1640 plus 5% fetal bovine serum, glutamine, penicillin, streptomycin and HEPES buffer). After washing, the cells are counted and set at a density of $1 \times 10^5$/ml. For culture, 0.2 ml of the cells are plated per well of a 96-well microtiter plate. The peptide or conjugate is added to the wells in a 50 ul volume that can be either filter or UV sterilized. The typical timing for this experiment is to expose the cells to the Apo E polypeptide or self-conjugate over night. PHA, the mitogen that stimulates lymphocyte growth and proliferation, is added the next day. Forty-eight hours after the addition of PHA, 1 uCi of $^3$H-thymidine is added per well in a 1 ul volume and 18-24 hours later the cells are harvested on a mash. The mash cell harvester functions to collect the cells on filter paper where they are washed with buffer to remove free $^3$H-thymidine. The filter papers are dried, put into scintillation vials with scintillation cocktail and the B emissions obtained.

When examined in the above-described assay, the polypeptides shown in Table 2 had no effect on lymphocyte proliferation when used in non-conjugated, monomeric form. However, as shown in FIG. 1, when those same polypeptides were used conjugated to bovine serum albumin (BSA), lymphocyte proliferation was apparently inhibited in an equivalent manner by all peptides studies, as evidenced by decreasing amounts of thymidine uptake with increasing dose of conjugate.

Figure 2:
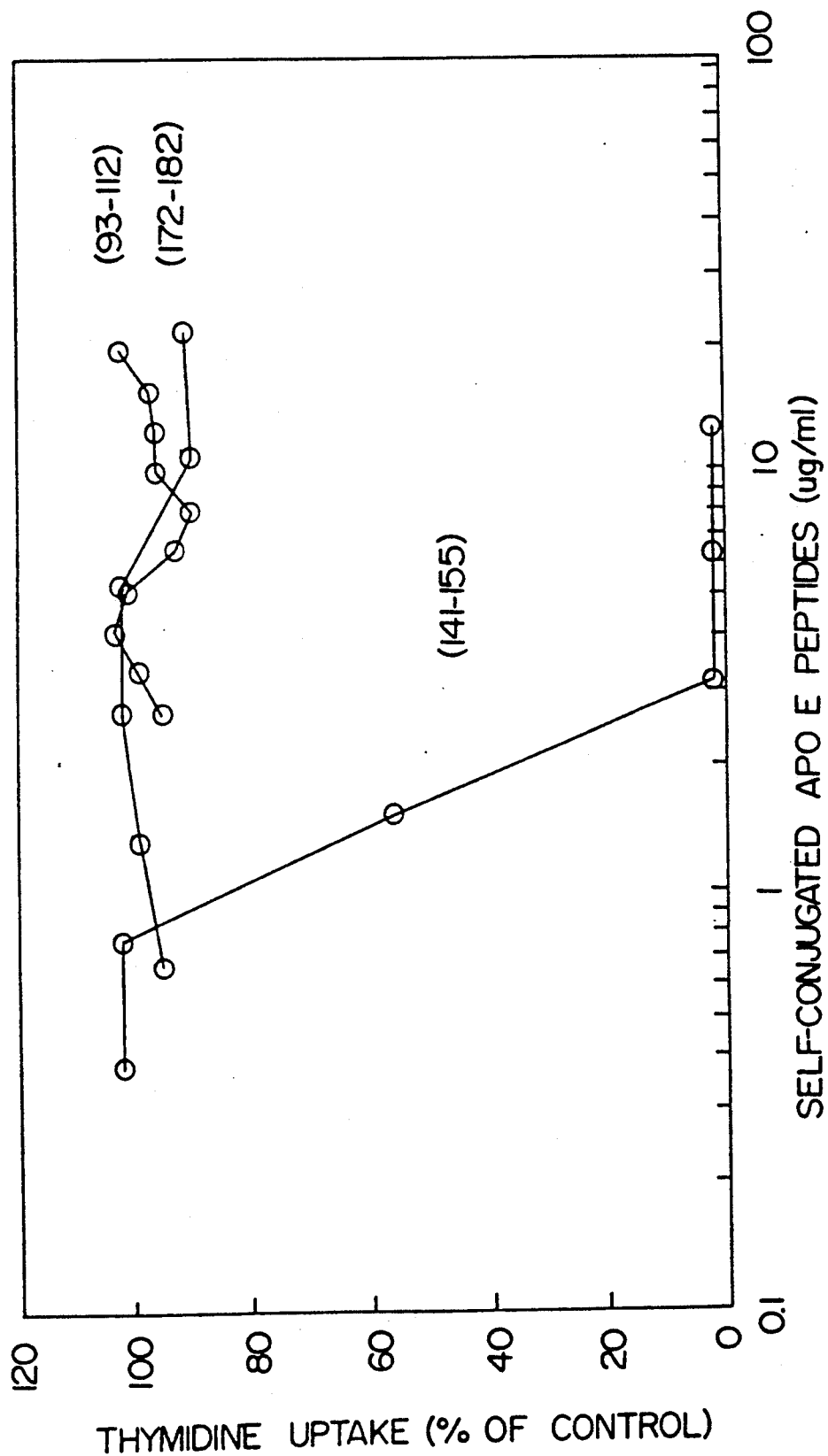
FIG. 2 illustrates that the inhibition of lymphocyte proliferation by self-conjugated Apo E-derived peptide p141-155 E was conjugate specific. Increasing concentrations of self-conjugates (p141-155)-(p141-155), (p172-182)-(p172-182) and (p93-112)-(p93-112) were added to cultures that contained $1 \times 10^6$ peripheral blood mononuclear cells per ml. The cells were cultured at 37° C. in RPMI with 5% serum. All cells were exposed to PHA at 24 hr, were labeled with $^3$H-thymidine at 48 hr. and were harvested at 72 hr. Control cells incorporated 124,130 cpm±4539. This value represents 100%.

3. Multimeric Peptides And Peptide Self-Conjugate's Specifically Inhibit Lymphocyte Proliferation In A Non-Cytotoxic Manner The ability of polypeptides and conjugates of this invention to specifically inhibit lymphocyte proliferation was examined using the assay described in Example 2. Specifically, self-conjugates (p172-182)-(p172-182), (p93-112)-(p93-112) and (p141-155)-(p141-155) were compared for the ability to inhibit lymphocyte proliferation. As shown in FIG. 2, self-conjugates (p172-182)-(p172-182) and (p93-112)-(p93-112) demonstrated no significant capacity to inhibit lymphocyte proliferation, as evidenced by their failure to reduce H$^3$-thymidine uptake. In contrast, a self-conjugate of this invention, (p141-155)-(p141-155) began demonstrating significant inhibitory activity in the concentration range of about 0.8 to about 1.0 ug/ml.

Figure 3:
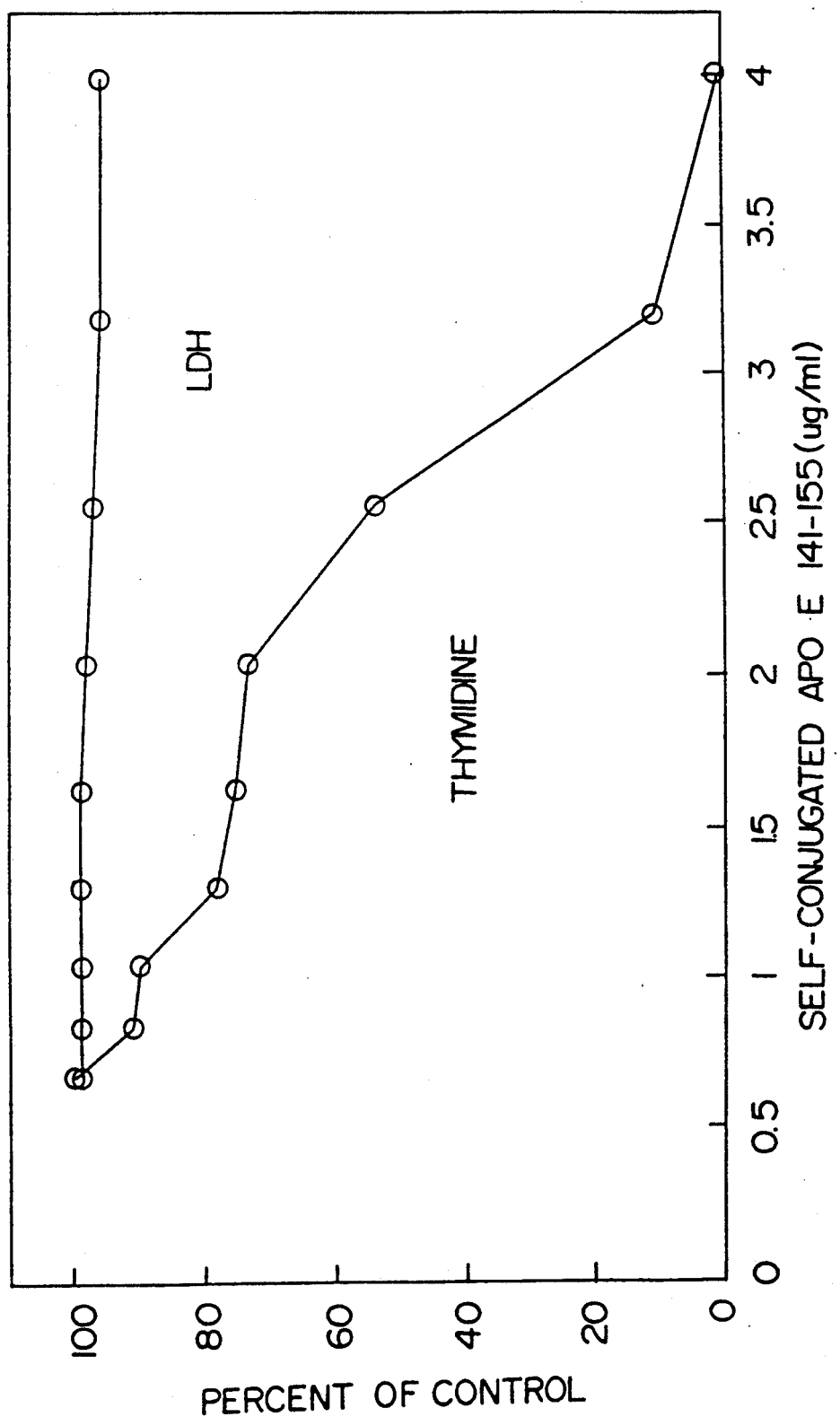
FIG. 3 illustrates that the inhibition of lymphocyte proliferation by self-conjugate (p141-155)- (p141-155) when added to cultures that contained $1 \times 10^6$ peripheral blood mononuclear cells per ml was not due to cytotoxicity. The cells were cultured at 37° C. in RPMI with 5% fetal bovine serum. All cells were exposed to PHA at 24 hr, were labeled with $^3$H-thymidine at 48 hr and were harvested at 72 hr. Cell culture supernatants from duplicate wells were collected for assay of lactate dehydrogenase (LDH) activity according to the method of Carney et al., *J. Immunol.*, 134:1804, (1985). Data is expressed as percent of control. $^3$H-thymidine uptake and LDH activity of PBS-exposed control lymphocytes was 0.085 and 1.232 change in O.D. 340 nm/min, respectively. LDH activity was measured following lysis of the cells with $H_2O$. Each point represents the average value from 4 wells per treatment and the standard error was less than 10%.

To examine whether or not the observed inhibition of proliferation was due to cell death (direct cytotoxicity), the treated cell cultures were subjected to a lactate dehydrogenase (LDH) release assay as described by Carney et al., *J. Immunol.*, 134:1084, (1985). The presence of LDH in the cell culture supernatant indicates toxicity because it is released by cells that have lysed. According to the results of this study, shown in FIG. 3 for self-conjugate (p141-155)-(p141-155), there is less than 4% release of LDH activity at the concentration of self-conjugate that inhibits lymphocyte proliferation by greater than 95%. These results demonstrate that the polypeptides and self-conjugates of this invention are not directly cytotoxic and inhibit lymphocyte proliferation specifically.

Inhibition by Apo E of mitogen-stimulated lymphocyte proliferation is not readily reversible. The reversibility of the inhibition by the self-conjugated peptides of this invention was tested by incubating lymphocytes overnight with the peptides, then washing the cultures before adding PHA. As shown in Table 3 the self-conjugate (p141-155) - (p141-155), was maximally inhibitory under these conditions. Further, this inhibitory activity could not be reversed by washing away the non-cell-associated self-conjugate peptide prior to PHA stimulation. In this respect, the inhibitory activity of self-conjugate (p141-155) -(p141-155) mimicked the irreversible inhibitory activity observed with native Apo E.

TABLE 3

| | 3H-Thymidine Uptake (cpm ± SD) | |
|---|---|---|
| Treatment | No Washing | |
| PBS | 69,106 ± 6,555 | 57,123 ± 8,842 |
| Self-conjugated apo E$_{141-155}$[c] | 1,035 ± 170 | 425 ± 100 |
| Self-conjugated apo A - I$_{95-105}$[c] | 83,480 ± 4,027 | 64,524 ± 4,200 |

Lymphocyte Proliferation was Irreversibly Inhibited by a Self-Conjugate of Peptide 141-155[a]

[a]All cultures contained $1 \times 10^6$ PBM cells per ml. The cells were cultured at 37° C. in RPMI 1640 with 5% fetal bovine serum. All cells were exposed to PHA at 24 hr., labeled with $^3$H-thymidine at 48 hr. and harvested at 72 hr.
[b]At 24 hr. the cells were washed three times in medium and resuspended to their original volume in RPMI 1640 containing 5% serum.
[c]Peptides were used at a final concentration of 40 μg/ml.

4. Monomeric Peptides And Peptide-BSA Conjugates Do Not Specifically Inhibit Ovarian Androgen Production The cell system used to examine the effect of various peptides and conjugates on ovarian androgen production was that described by Curtiss et al., *J. Biol. Chem.*, 263:10965, (1988). Briefly, hypophysectomized (pituitary removed) immature female rats are sacrificed by cervical dislocation. The ovaries taken from the rats are trimmed free of fat and other non-ovarian tissues, cut into approximately six to eight pieces per ovary and dissociated in a solution of collagenase/ DNAase which degrades the connective tissue releasing cell clusters. Approximately one to two hours of 37° C. incubation is required to dissociate the tissue. The cells are washed three times with fresh McCoy's 5A modified medium supplemented with glutamine and penicillin/streptomycin. No serum is added to this medium. The cells are cultured over night in 10 ml of medium in a T-25 flask to allow the non-steroidogenic cells to adhere. The next day non-adherent cells are recovered, washed three times with fresh media, counted and plated at a density of $1 \times 10^3$/ml aliquotting 0.2 ml per well of a 96-well microtiter plate. All media in the experiment contains luteinizing hormone (LH) at 4 ng/ml and human high density lipoprotein (HDL) at 300 ug protein/ml. Monomeric peptides, peptide-BSA conjugates and self-conjugated peptide preparations are added in a 50 μ37 μl volume in PBS. The cells are cultured for 48 hours then the supernatants are recovered, transferred to a clean 96-well microtiter plate and kept at −20° C. until the concentrations of androstenedione and progesterone are measured by radioimmunoassay.

Figure 4:
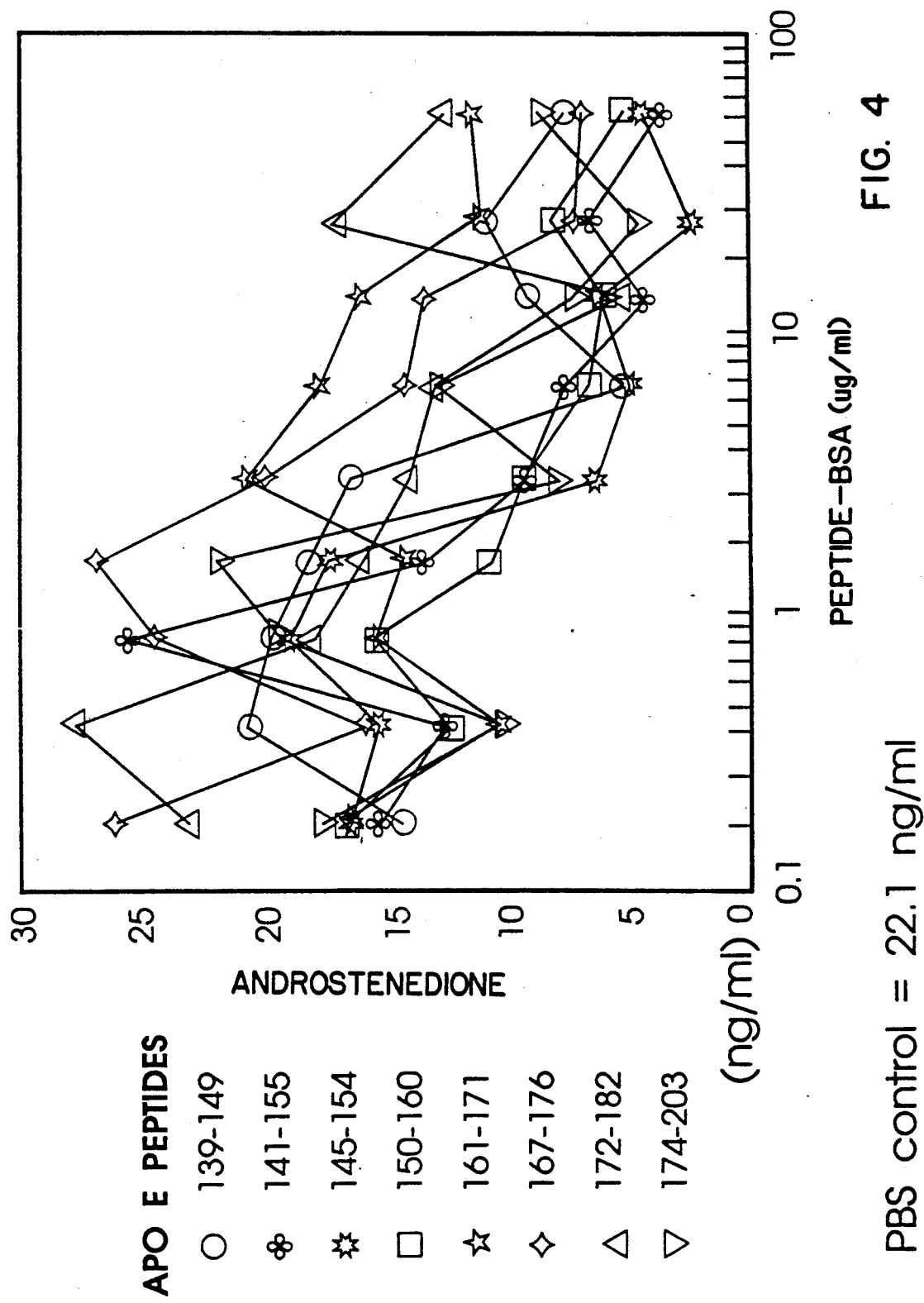
FIG. 4 illustrates that all Apo E peptide-BSA conjugates inhibited ovarian androgen production in an approximately equivalent manner, thereby indicating a lack of specificity. Increasing concentrations of Apo E peptide-BSA conjugates were added to ovarian cells $(1 \times 10^5/ml)$ that were cultured at 37° C. in serum-free McCoy's 5a modified medium containing 4 ng/ml of LH and 300 ug/ml of human HDL. After 48 hr of culture the supernatants were collected and the androstenedione concentration measured by radioimmunoassay. Each point represents the average androstenedione concentration from 4 wells per treatment and the standard error was less than 10% for all points.

When examined in the above-described assay, all of the polypeptides of Table 2 that were studied, when used in non-conjugated, monomeric form, had no effect on androgen secretion. However, as shown in FIG. 4, when those same peptides were used conjugated to BSA, androgen production was apparently inhibited in an equivalent manner by all peptides studied, as evidenced by decreasing amounts of androstenedione production with increasing dose of conjugate.

Figure 5:
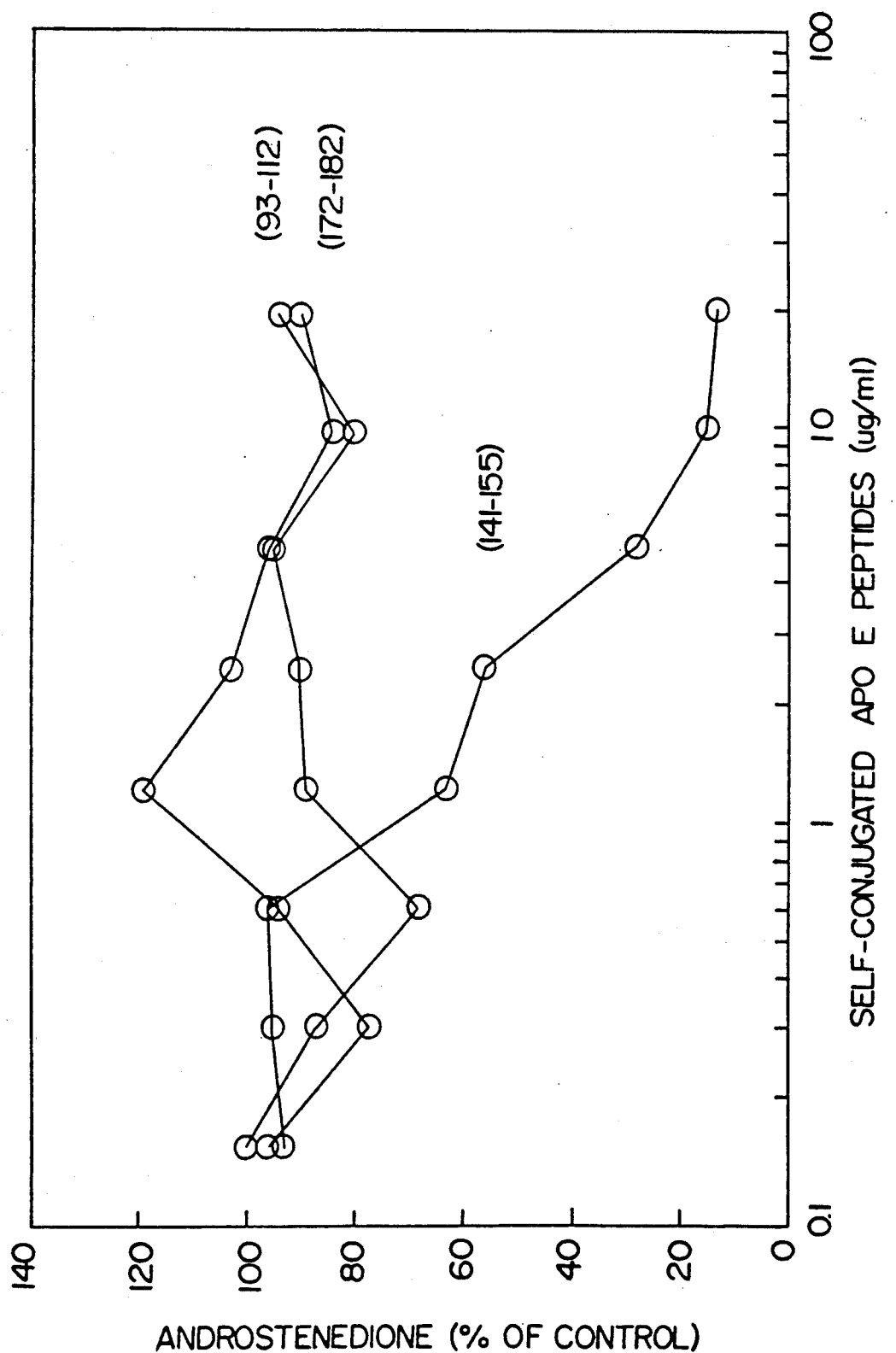
FIG. 5 illustrates that the inhibition of ovarian androstenedione production by self-conjugated Apo E-derived peptide (p141-155) was conjugate specific. Increasing concentrations of selfconjugates (p141-155) - (p141-155), (p172-182)-(p172-182) and (p93-112) - (p93-112) Were added to ovarian cells $(1 \times 10^5/ml)$ that were cultured at 37° C. in serum-free McCoy's 5a medium containing 4 ng/ml of LH and 300 μg/ml or human HDL. After 48 hours of culture, the supernatants were collected and the androstenedione concentration measured by immunoassay. Each point represents the average androstenedione concentration from four wells per treatment. Standard deviation was less than 10% for all means.
Figure 6:
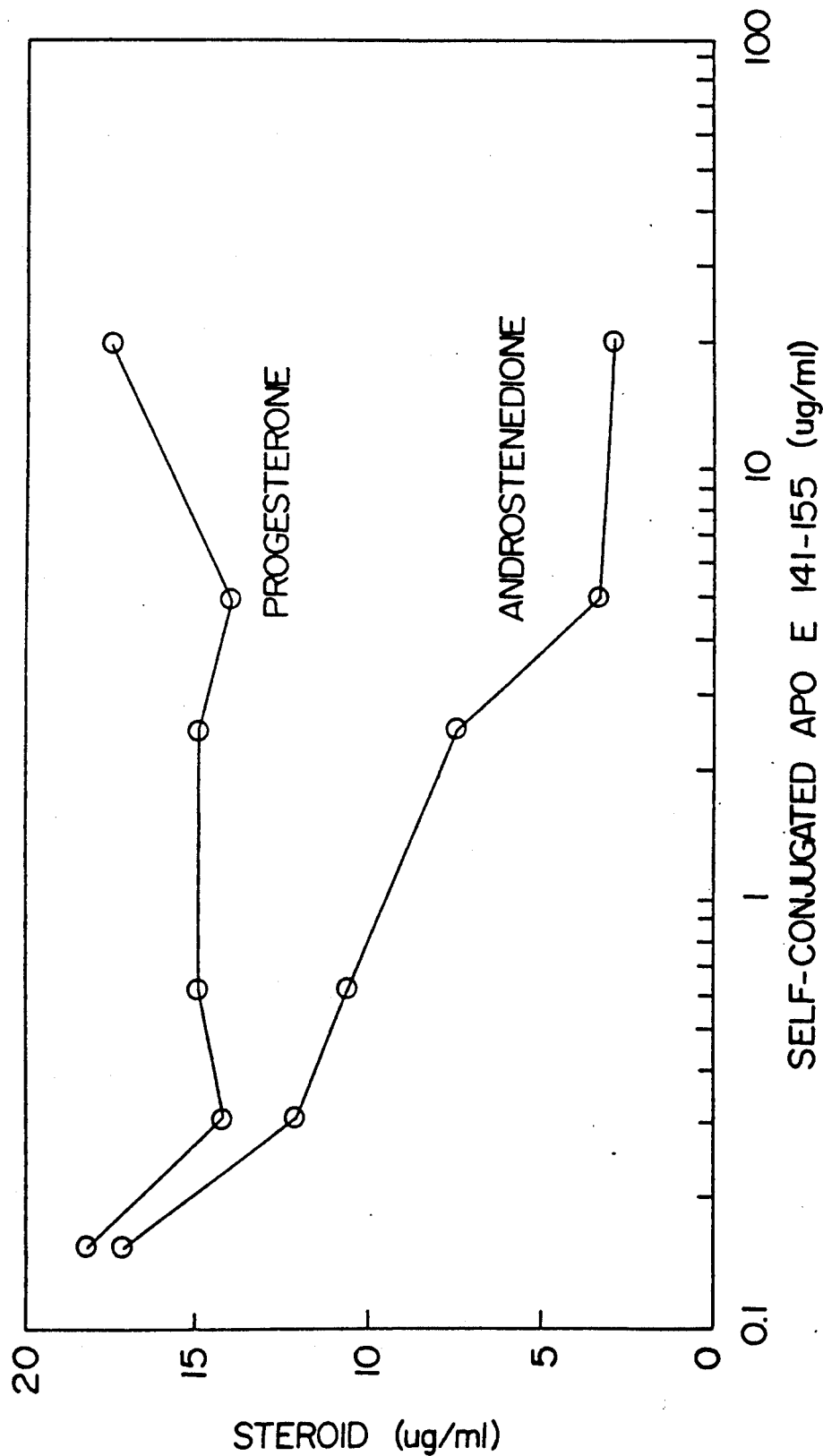
FIG. 6 illustrates that ovarian androstenedione production was specifically inhibited by self-conjugate (p141-155)-(p141-155) without causing direct cellular toxicity. Increasing concentrations of self-conjugate (p141-155)-(p141-155) were added to ovarian cells $(1 \times 10^5/ml)$ that were cultured at 37° C. in serum-free McCoy's 5a medium containing 4 ng/ml of LH and 300 ug/ml of human HDL. After 48 hr of culture the supernatants were collected and androstenedione and progesterone concentrations measured by radioimmunoassay. Each point represents the average of steroid concentrations from 4 wells per treatment and the standard error was less than 10% for all points.

5. A Multimeric Peptide And A Peptide Self-Conjugate Specifically Inhibit Ovarian Androgen Production The ability of polypeptides and conjugates of this invention to specifically inhibit ovarian androgen production was examined using the assay described in Example 4. As shown in FIG. 5, self-conjugate (p141-155)-(p141-155) demonstrated the ability to inhibit androgen production in ovarian theca/interstitial cells at a concentration as low as that in the range of about 1.5 $\mu$/ml. In contrast, other self-conjugates not containing the Apo E 141-155 do not inhibit androgen production.

Apo E inhibition of ovarian cell androstenedione production is reversible. To test if the inhibitory activity of self-conjugate (P141-155)-(P141-155) was reversible, ovarian cells were cultured with the peptide for 48 hours. At the end of this culture, the medium was removed and replaced with fresh medium without the self-conjugated peptide. As shown in Table 4, ovarian androstenedione production was inhibited during the first 48 hours of culture but, after the peptide was removed and the ovarian cells refed with fresh medium, their androstenedione production during the subsequent 48 hours returned to control levels. In this respect, the activity of the polypeptides and/or conjugates of the present invention mimicked the activity of the native APO E.

TABLE 4

| Ovarian Androgen Production was Reversibly Inhibited by a Self-Conjugate of Apo E Peptide 141-155[a] | | |
|---|---|---|
| | Androstenedione Accumulation (ng/ml) | |
| Treatment | First 48 hr. of Culture | Second 48 hr. of Culture |
| PBS | 12.13 ± 0.26 | 11.27 ± 0.84 |
| Self-conjugated Peptide | 6.27 ± 1.26 | 13.34 ± 2.75 |

[a]Ovarian theca/interstitial cells (20,000/0.25 ml) were cultured in the absence or presence of self-conjugated peptide. After 48 hr. of culture the supernatants were removed and the cells refed with fresh medium without self-conjugated peptide.

To examine whether or not the observed inhibition of androgen production was due to cell death (cytotoxicity), the treated cell cultures were assayed for progesterone production as described by Dyer et al., *J. Biol. Chem.*, 263:10965-10973, (1988). The presence of progesterone in the culture indicates the cell are viable. According to the results of this study, also shown in FIG. 5 for self-conjugate (p141-155)-(p141-155), there is no significant decrease in progesterone production at the concentration of self-conjugate that inhibits 95% of androstenedione (Adione) production. This result indicates that the observed inhibitory activity was specific and not the result of cell death (cytotoxicity).

Figure 7:
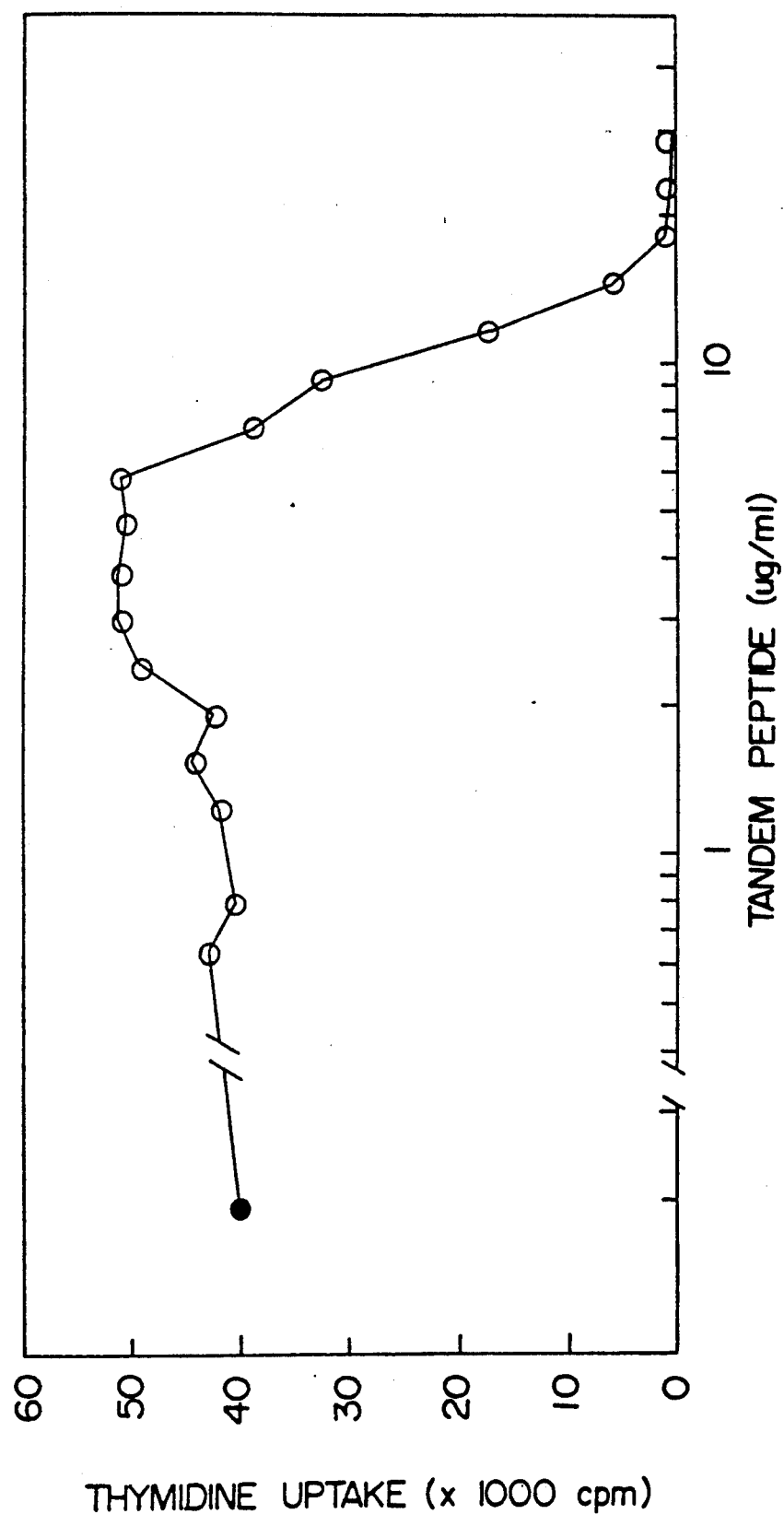
FIG. 7 illustrates that the tandem Apo E peptide p(141-155) affects lymphocyte proliferation in a dose dependent, bi-phasic manner. Increase in concentrations of tandem Apo E peptide were added to cultures that contained $8 \times 10^5$ peripheral blood mononuclear cells per ml. The cells were cultured at 37° C. and RPMI with 5% serum. All cells were exposed to PHA at 24 hours, labeled with 33H-thymidine at 72 hours and harvested at 90 hours. The data points represent the mean of four wells per treatment. The standard deviation was less than 10% for all means.
Figure 8:
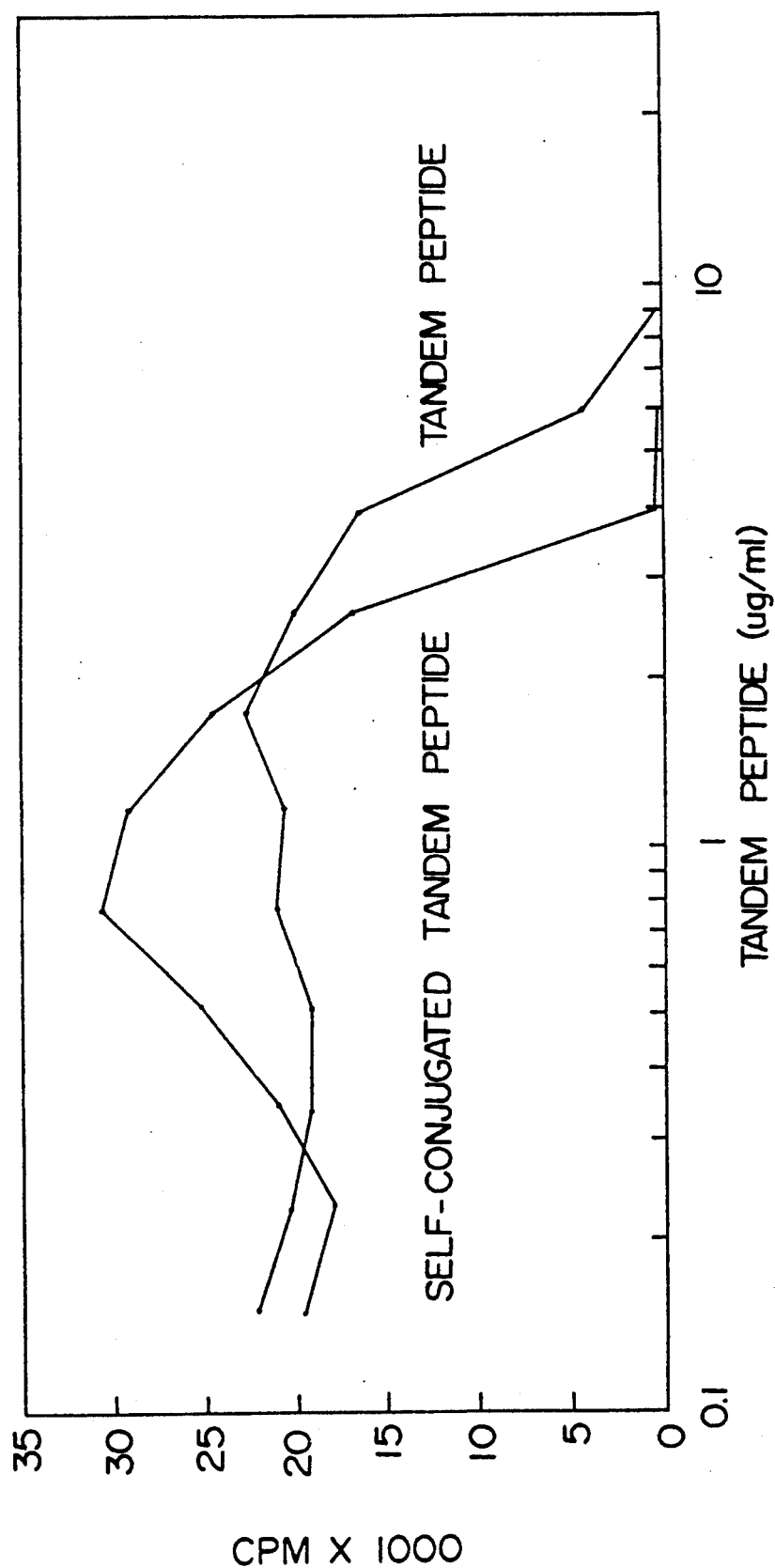
FIG. 8 illustrates that lymphocyte proliferation was inhibited more strongly by self-conjugate of the tandem Apo E peptide $p(141-155)_2-p(141-155)_2$ (than by tandem peptide $p(141-155)_2$ when) added to cultures that contain $8 \times 10^5$ peripheral blood mononuclear cells per ml. The cells were cultured at 37° C. in RPMI with 5% fetal bovine serum. All cells were exposed to PHA at 24 hours, labeled with 3H-thymidine at 72 hours and harvested at 90 hours. The data points represent the mean of 4 wells per treatment. Standard deviation was less than 10% for all means.

6. A Dimeric Peptide and Self-Conjugates of the Dimeric Peptide Affect Lymphocyte Proliferation The ability of the Dimeric Peptide p(141-155)$_2$ and self-conjugates of this peptide p(141-155)$_2$ - p(141-155)$_2$ to affect lymphocyte proliferation was examined using the assay described in Example 2. As shown in FIG. 7, tandem Apo E peptide p(141-155)$_2$ enhanced lymphocyte proliferation at low concentrations and inhibited lymphocyte proliferation at high concentrations. This ability to both enhance and inhibit lymphocyte proliferation, depending upon the dose of the peptide, mimics the activity of the native Apo E. Enhancement of lymphocyte proliferation was seen at doses of tandem Apo E peptide from about 2 $\mu$g/ml to about 6 $\mu$g/ml, while inhibition of proliferation was seen at concentrations of at least 8 $\mu$g/ml. As shown in FIG. 8, self-conjugates of tandem Apo E peptide were even more potent than tandem Apo E peptide alone in its ability to affect lymphocyte proliferation.

Figure 9:
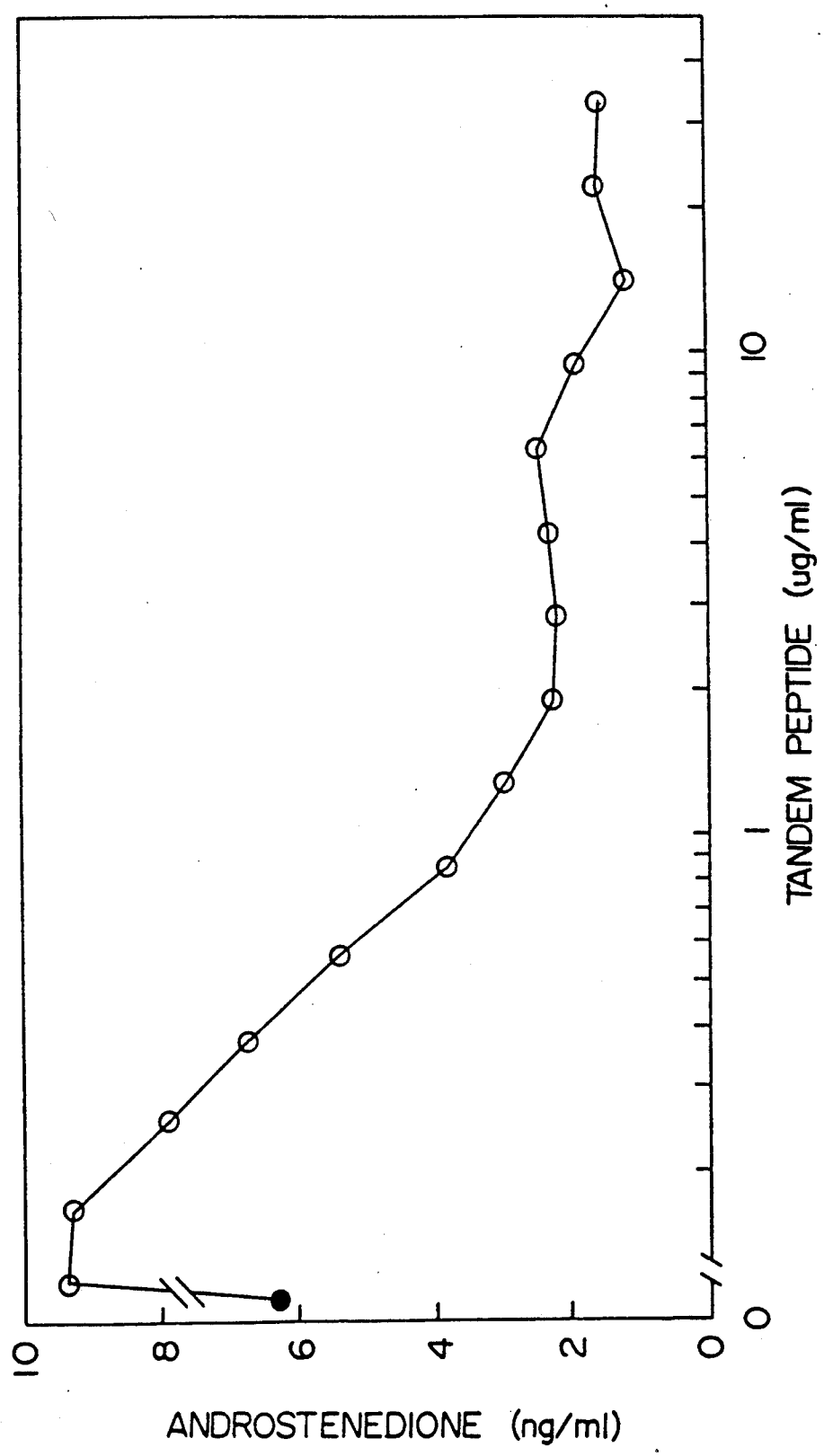
FIG. 9 illustrates that tandem Apo E peptide $p(141-155)_2$ affects ovarian androstenedione production in a dose-dependent, bi-phasic manner. Increasing concentrations of tandem Apo E peptide were added to ovarian cells $(8 \times 10^4/mil)$ that were cultured at 37° C. in serum-free McCoy's 5a modified medium containing 4 ng/ml of LH and 300 μ/ml of human HDL. After 48 hours of culture, the supernatants were collected, and the androstenedione concentration measured by radioimmunoassay. The data points are the mean steroid concentration of four wells per treatment. The standard deviation was less than 10% for all means.

7. A Dimeric Peptide and Self-Conjugates of this Peptide Affect Ovarian Androgen Production The ability of tandem Apo E peptide and self-conjugates of this peptide to affect ovarian androgen production was examined using the assay described in Example 4. As shown in FIG. 9, when tandem Apo E peptide was added in concentrations less than about 0.4 $\mu$g/ml, androstenedione production was enhanced. Concentrations of tandem Apo E peptide greater than about 0.6 $\mu$g/ml inhibited androstenedione production in a dose-dependent manner.

8. A Dimeric Peptide Affects LDL Binding and Degradation

Figure 10:
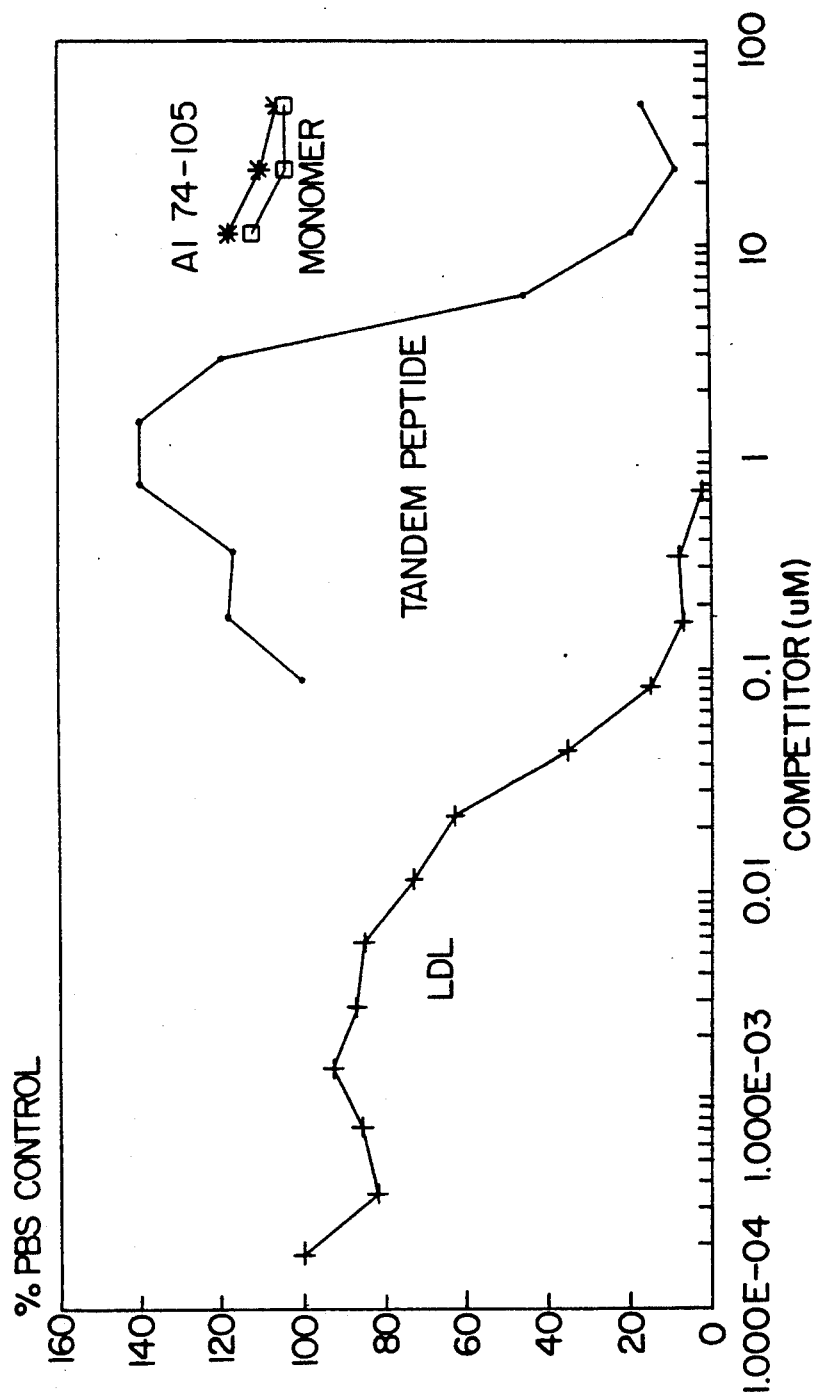
FIG. 10 illustrates that tandem Apo E peptide $p(141-155)_2$ affects LDL binding and degradation in a dose dependent, biphasic manner. Increasing concentrations of tandem Apo E protein were added to cultures of THP-1 cells simultaneously with the addition of $^{125}$I-LDL. The disappearance of acid soluble $^{125}$I-LDL was followed over a five-hour incubation at 37° C. Also shown are dilutions of LDL (+), MONOMER ( ), and peptide A1 74-105 (*). Each point represents the average radioactivity from 4 wells per treatment. Standard deviation was less than 10% for all means.
Figure 11:
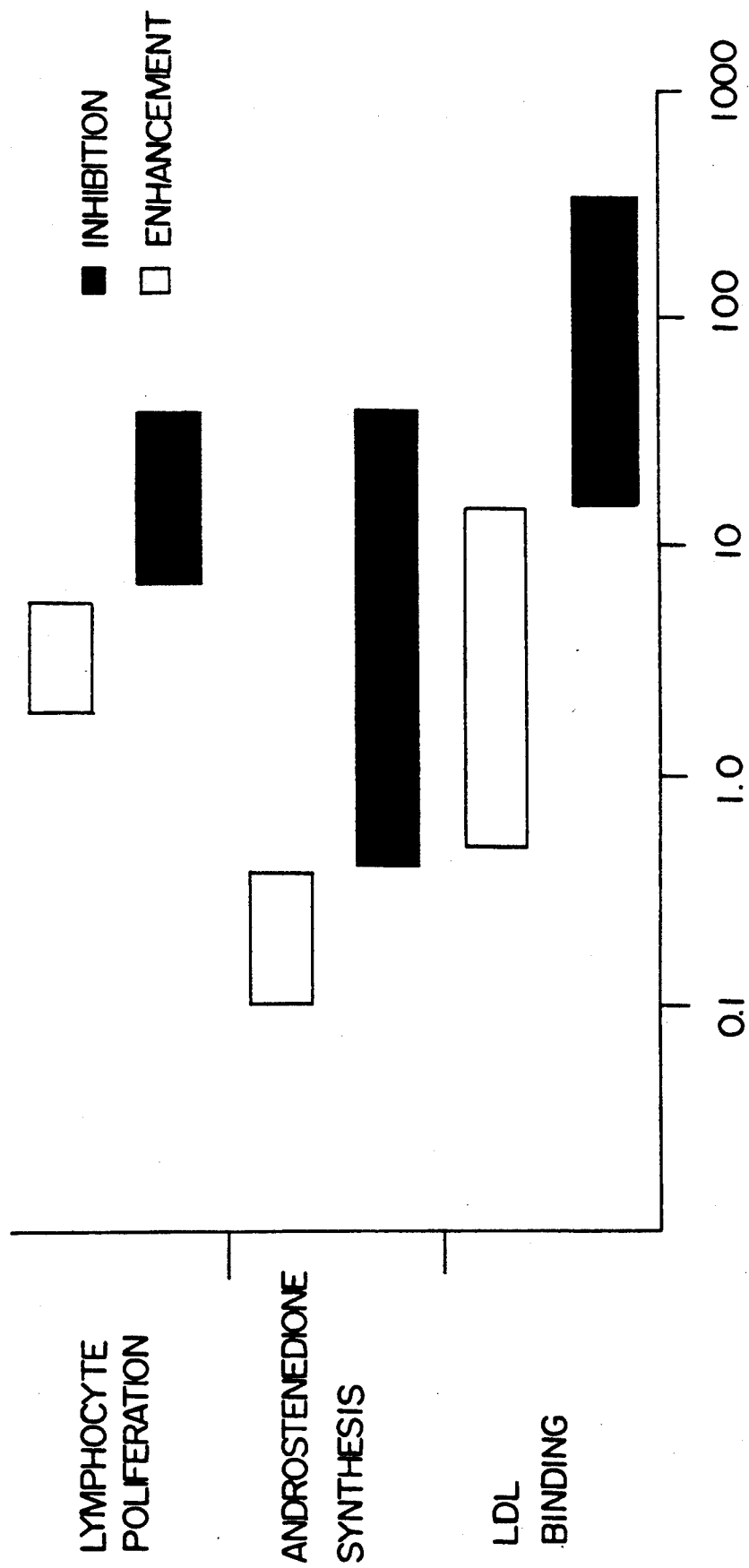
FIG. 11 summarizes the in vitro effects of tandem Apo E peptide p(141–155)$_2$ at the indicated concentration ranges (ug/ml) on lymphocyte proliferation, ovarian androgen production and LDL binding. These data can serve as a model for the in vivo determination of the appropriate amount of peptide and/or conjugate to be administered based on the desired therapeutic effect, e.g. hepatic LDL uptake (degradation).

An established cell line, THP-1 was used to examine the ability of tandem Apo E peptide to enhance the binding and degradation of LDL. THP-1 cells, differentiated into a macrophage-like stage (Hara, H. et al., *Biochem. Biophys. Res. Comm.*, 146(2):802-808, (1987) were preincubated for 24 hours at 37° C. in RPMI 1640 medium containing 10% lipoprotein-deficient serum supplemented with penicillin (100 mg/ml). Binding and degradation of LDL was evaluated as the disappearance of acid soluble $^{125}$I-LDL radioactivity from the incubation over a 5-hour incubation at 37° C. Various concentrations of unlabeled LDL or tandem Apo E peptide were coincubated with the $^{125}$I-LDL to determine their effects on binding and degradation. As shown in FIG. 10, tandem Apo E peptide enhanced LDL degradation at low concentrations and inhibited LDL degradation at high concentrations. In this experiment, enhancement of LDL concentration occurred at tandem Apo E peptide concentrations ranging from about 0.08 to about 1.5 $\mu$M. Inhibition of LDL degradation began to occur at tandem Apo E peptide levels of 2.0 to 5.0 $\mu$M. Unlabeled LDL inhibited $1^{125}$I-LDL degradation, indicating the specificity of the LDL-receptor.

The foregoing specification, including the specific embodiments and examples, is intended to be illustrative of the present invention and is not to be taken as limiting. Numerous other variations and modifications can be effected without departing from the true spirit and scope of the invention.

What is claimed:

1. A composition for modulating hepatic uptake of low density lipoprotein comprising a therapeutically effective amount of a polypeptide having an LDL-receptor binding segment and an LDL binding segment, said LDL-receptor binding segment having an amino acid residue sequence represented by the formula:

Leu-Arg-Lys-Leu-Arg-Lys-Arg-Leu-Leu-Arg-Asp-

Ala-Asp-Asp-Leu-Leu-Arg-Lys-Leu-Art-Lys-Arg-

Leu-Leu-Arg-Asp-Ala-Asp-Asp-Leu, and said LDL binding segment having an amino acid residue sequence represented by the formula:
Glu-Trp-Leu-Lys-Ala-Phe-Tyr-Glu-Lys-Val-Leu-Glu-Lys-Leu-Lys-Glu-Leu-Phe, and a suitable carrier therefor.

* * * * *

UNITED STATES PATENT AND TRADEMARK OFFICE
CERTIFICATE OF CORRECTION

PATENT NO. : 5,182,364

DATED : January 26, 1993

INVENTOR(S) : Dyer, et al.

It is certified that error appears in the above-identified patent and that said Letters Patent is hereby corrected as shown below:

In Column 1, line 4, insert:

-- This invention was made with government support under Grant No. HL 35297 awarded by the National Institutes of Health. The government has certain rights in the invention. --

Signed and Sealed this

Eighteenth Day of January, 1994

Attest:

BRUCE LEHMAN

*Attesting Officer*   *Commissioner of Patents and Trademarks*